United States Patent [19]

Iinuma

[11] Patent Number: 4,485,821
[45] Date of Patent: Dec. 4, 1984

[54] DOPPLER EFFECT BLOOD FLOW SENSING DEVICE DISPLAYING SIGNALS LYING WITHIN A BAND WIDTH RELATED TO SAMPLING FREQUENCY

[75] Inventor: Kazuhiro Iinuma, Sendai, Japan

[73] Assignee: Tokyo Shibaura Denki Kabushiki Kaisha, Kawasaki, Japan

[21] Appl. No.: 411,553

[22] Filed: Aug. 25, 1982

[30] Foreign Application Priority Data

Aug. 28, 1981 [JP] Japan ................. 56-135104

[51] Int. Cl.³ ............................................ A61B 10/00
[52] U.S. Cl. ..................................................... 128/663
[58] Field of Search ..................... 128/663; 73/861.25

[56] References Cited

U.S. PATENT DOCUMENTS 3,896,788  7/1975  Sato ..................................... 128/663
4,318,413  3/1982  Iinuma ................................. 128/663

FOREIGN PATENT DOCUMENTS 4257278  3/1981  European Pat. Off. .
10304    4/1980  Japan .
35213    9/1981  Japan .

Primary Examiner—Kyle L. Howell
Assistant Examiner—Deidre Foley
Attorney, Agent, or Firm—Cushman, Darby & Cushman

[57] ABSTRACT

A pulsed ultrasound Doppler blood flow sensing device includes a band pass filter for extracting only the Doppler frequency shift signals from the sampled and held signals, the band pass filter having a band pass characteristic in which a variation of an attenuation degree is almost flat over at least a frequency band between $-f_r/2$ and $+f_r/2$ except for a region in proximity to frequency O. A display displays blood flow signals which represent the obtained Doppler frequency shifts and have frequencies at least between the frequencies $-f_r$ and $+f_r$.

3 Claims, 5 Drawing Figures

DOPPLER EFFECT BLOOD FLOW SENSING DEVICE DISPLAYING SIGNALS LYING WITHIN A BAND WIDTH RELATED TO SAMPLING FREQUENCY

BACKGROUND OF THE INVENTION

The present invention relates to a pulsed ultrasound Doppler blood flow sensing device of the type in which ultrasound pulses are emitted from a transducer at a fixed rate frequency into an organism, echoes from blood corpuscles are received by the transducer, Doppler frequency shifts of the ultrasound pulses are detected from the echoes, and a blood flow is displayed by a display device.

The pulsed ultrasound Doppler blood flow sensing device measures a blood flow by making use of a proportional relation of the blood flow to the Doppler frequency shift.

Generally, the Doppler frequency shift $f_d$ is given by the following equation $$f_d = \frac{2V \cos\theta}{C} f_c$$

Where
$f_c$: Frequency of a ultrasonic pulse radiated toward a moving object,
V: Velocity of the moving object which refelects the ultrasound pulses,
$\theta$: Angle of the ultrasonic pulse to the moving direction of the moving object,
C: Propagation velocity of the ultrasound pulse.

From the above equation, it is seen that the Doppler frequency shift $f_d$ is proportional to the velocity of the moving object. The pulsed ultrasound Doppler blood flow sensing device depends on the above relation of the Doppler frequency shift to the velocity of the moving object. In the blood flow sensing device, ultrasound pulses are radiated from a transducer at a fixed rate frequency or a fixed sampling frequency. Echoes of the radiated ultrasound pulses from blood corpuscles (the moving object) are received by the transducer to obtain the Doppler frequency shifts of the ultrasound pulse on the basis of the frequencies of the echoes. The blood flow is measured on the basis of the Doppler frequency shifts.

The sampling theorem describes that the upper limit of the Doppler frequency shift is ½ of the sampling rate frequency $f_r$. For this reason, the prior device converts the received echoes into electrical signals (echo signals), passes the component of the echo signals coming from the corpuscles in the blood flowing in a toward (+) direction through a band pass filter with a frequency band from 0 to $f_r/2$ and analyzes the frequency of the signal passed through the filter. The component of the echo signals of the corpuscles in the blood flowing in an away (−) direction is passed through a band pass filter of 0 to $f_r/2$ and the frequency of the signal passed through the filter is analysed. Only the signal as shown in FIG. 1 within a frequency range between $+f_r/2$ and $-f_r/2$ is displayed as the blood flow signal Incidentally, the term "toward" direction means the direction of the blood flow flowing toward the ultrasound source or the transducer, and the "away" direction is opposite to the "toward" direction.

The band pass filters assembled into the prior blood flow sensing device have each a frequency characteristic in which the attenuation degree is extremely large in the vicinity of the frequency of $|f_r|/2$, as shown in FIG. 2. Accordingly, the prior device displays only the blood flow signals that fall within a frequency band defined by $\pm f_r/2$, and cannot display the blood flow signal at a frequency exceeding $\pm f_r/2$. Therefore, it is difficult to correctly recognize the blood flow signal.

SUMMARY OF THE INVENTION

Accordingly, the object of the present invention is to provide a pulsed ultrasound Doppler blood flow sensing device which can display a blood flow signal at frequencies exceeding $\pm f_r/2$ in a continuous manner.

To achieve the above object, there is provided a pulsed ultrasound Doppler blood flow sensing device comprising: rate pulse signal generating means for producing a rate pulse signal at a rate frequency; drive pulse signal generating means for producing a drive pulse signal in response to the rate pulse signal; transducing means for emitting ultrasound pulses into an object under diagnosis in response to a drive pulse signal from the drive pulse signal generating means and for converting echoes of the ultrasonic pulses returning from the object into electrical signals; sampling and holding means for sampling and holding only the electrical signals of echoes returning from positions at a given depth of the object; band pass filter means for extracting only the Doppler frequency shift signals from the sampled and held signals, the band pass means having a band pass characteristic in which a variation of an attenuation degree is almost flat over a frequency band at least between $-f_r/2$ and $+f_r/2$ except for a region in proximity to frequency 0; frequency analyzing circuit for analyzing the frequencies of the Doppler frequency shift signals; signal processing means for processing the frequency analyzed Doppler frequency shift signals to obtain Doppler shifts; and display means for displaying blood flow signals which represents the obtained Doppler frequency shifts and have frequencies at least between the frequencies $-f_r$ and $+f_r$.

DETAILED DESCRIPTION OF THE PREFERRED EMBODIMENTS

Figure 3:
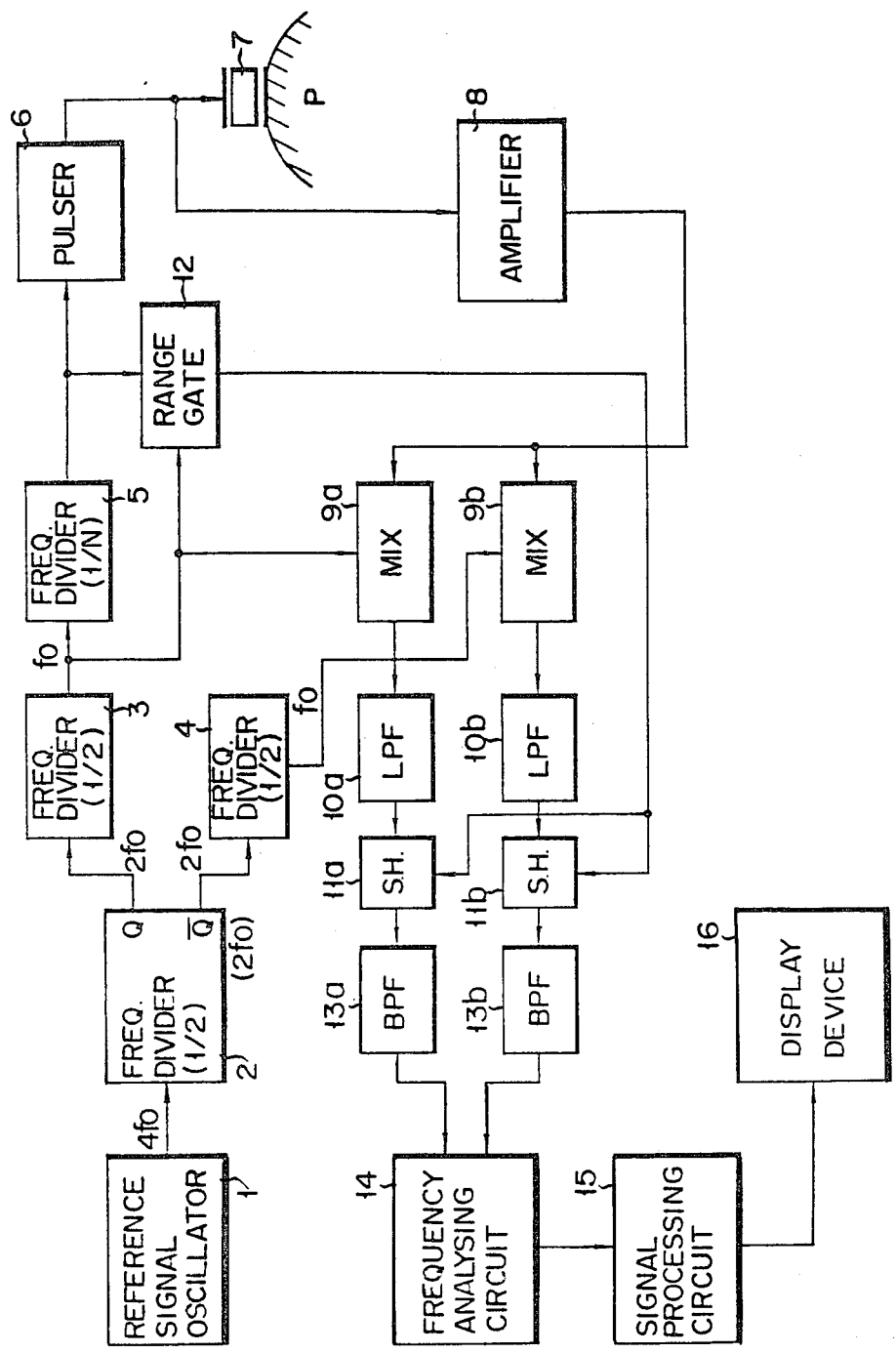
FIG. 3 is a block diagram of an embodiment of a pulsed ultrasonic Doppler flow sensing device according to the present invention.

Referring to FIG. 3, there is shown an embodiment of a pulsed ultrasound Doppler blood flow sensing device according to the present invention. In the figure, a reference signal oscillator 1 is a crystal oscillator for generating pulse signals with a stable frequency, for example, 10 MHz. The oscillator 1 is connected to an input terminal of a first frequency divider 2 for dividing the frequency of the pulse signal from the oscillator 1 in half. The frequency divider 2 is formed of a flip-flop circuit, for example. The output terminals Q and $\overline{Q}$ of the frequency divider 2 are connected to second and third frequency dividers 3 and 4 which further halves the frequency of the output signal from the first frequency divider 2. The second frequency divider 3 is connected to a fourth frequency divider 5 for dividing the frequency of the output signal from the second frequency divider 3 into 1/N frequency, and is further connected to the first input terminal of a range gate circuit 12. The output terminal of the fourth frequency divider 5 is connected to an input terminal of a pulser 6 and the second input terminal of the range gate circuit 12. The output terminal of the pulser 6, connected to an ultrasound transducer 7, receives the output signal from the fourth frequency divider 5 as a rate frequency signal to drive the transducer 7. The transducer 7, when disposed on an organism, emits ultrasound pulses into the organism and receives the echoes of the ultrasound pulses returned from the organism. The transducer 7 is connected to an amplifier 8 which amplifies the echo signal from the transducer 7. The output terminal of the amplifier 8 is connected to the first input terminals of first and second mixers 9a and 9b which receive the output signal from the amplifier 8 as a first input signal. The first mixer 9a is connected at the second input terminal to an output terminal of the second frequency divider 3, and receives the output signal from the second frequency divider 3 as a second input signal. The second mixer 9b is connected at the second input terminal to the output terminal of the third frequency divider 4 and receives the output signal from the third frequency divider 4 as a second input signal. These first and second mixers 9a and 9b each mix the first and second input signals. The output terminals of these mixers are respectively connected to the first and second low pass filters 10a and 10b. The output terminals of the low pass filters 10a and 10b are connected to first and second sample/hold (S/H) circuits 11a and 11b, respectively. The control terminals of the S/H circuits 11a and 11b are connected to the output terminals of the range gate circuit 12, and receive the output signal from the range gate circuit 12 as a control signal. The output terminals of the first and second S/H circuits 11a and 11b are connected to the input terminals of first and second band pass filters (BPF) 13a and 13b, respectively. The output terminals of the first and second BPFs 13a and 13b are connected to the first and second input terminals of a frequency analyzing circuit 14. The frequency analyzing circuit 14 is formed of a digital circuit (containing an analog to digital converter) using a high speed Fourier transform system. The output terminal of the frequency analyzing circuit 14 is connected to the input terminal of the signal processing circuit 15. The output terminal of the signal processing circuit 15 is connected to a display device 16.

Figure 4:
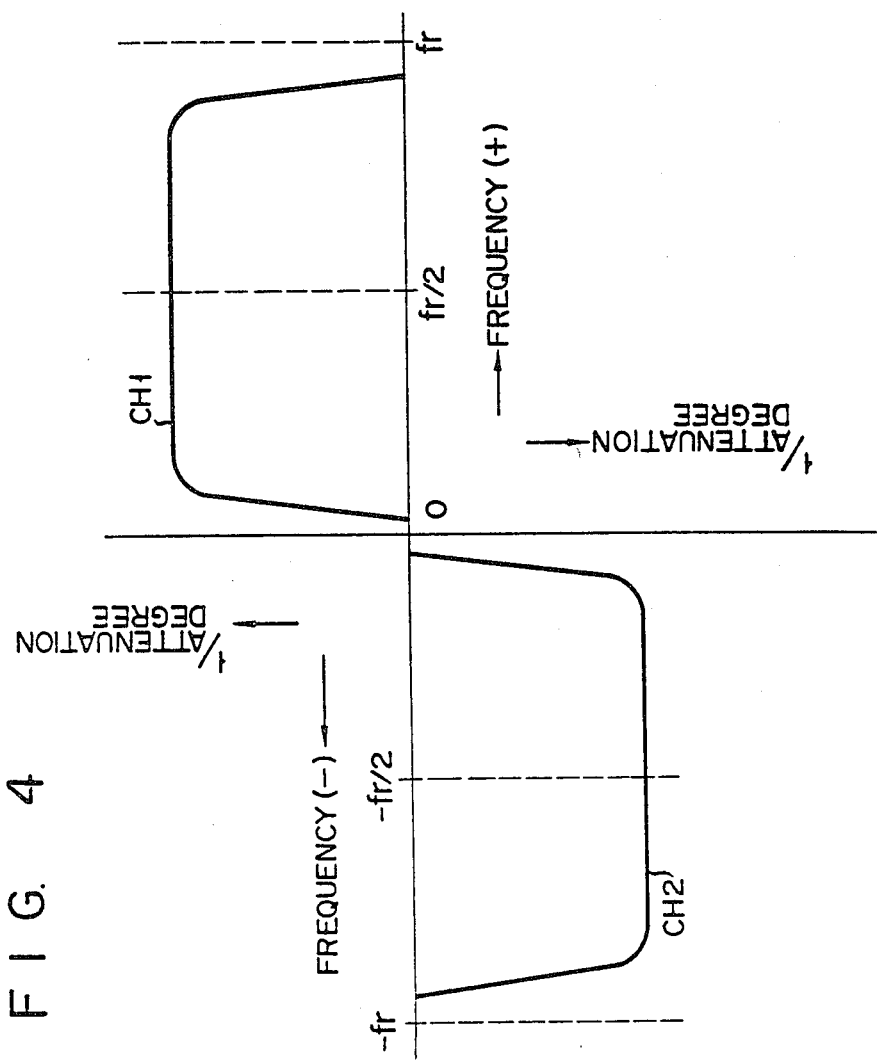
FIG. 4 shows the band pass characteristics of a band pass filter assembled into the sensing device shown in FIG. 3.

As shown in FIG. 4, the band pass filters 13a and 13b have a frequency characteristic such that a variation of an attenuation degree is almost flat over a frequency range from $-f_r$ to $+f_r$, except for the frequency regions in proximity to 0 and $\pm f_r$. In other words, the variation of the attenuation degree of the filter is substantially flat over the frequency range between $\pm f_r/2$ except the frequency region in the vicinity of frequency 0. This indicates that the display device 16 can display the blood flow signals with frequencies within at least the frequency range between $\pm f_r$.

The mixer 9a, the low pass filter 10a, the sample/hold circuit 11a and the band pass filter 13a forms a circuit for detecting the component of the echo signals coming from the corpuscles in the blood flowing in the toward (+) direction. Similarly, the mixer 9b, the low pass filter 10b, the sample/hold circuit 11b and the band pass filter 13b forms a circuit for detecting the component of the echo signals coming from the corpuscles in the blood flowing in the away (−) direction.

The blood flow sensing device with such an arrangement will be described.

Figure 1:
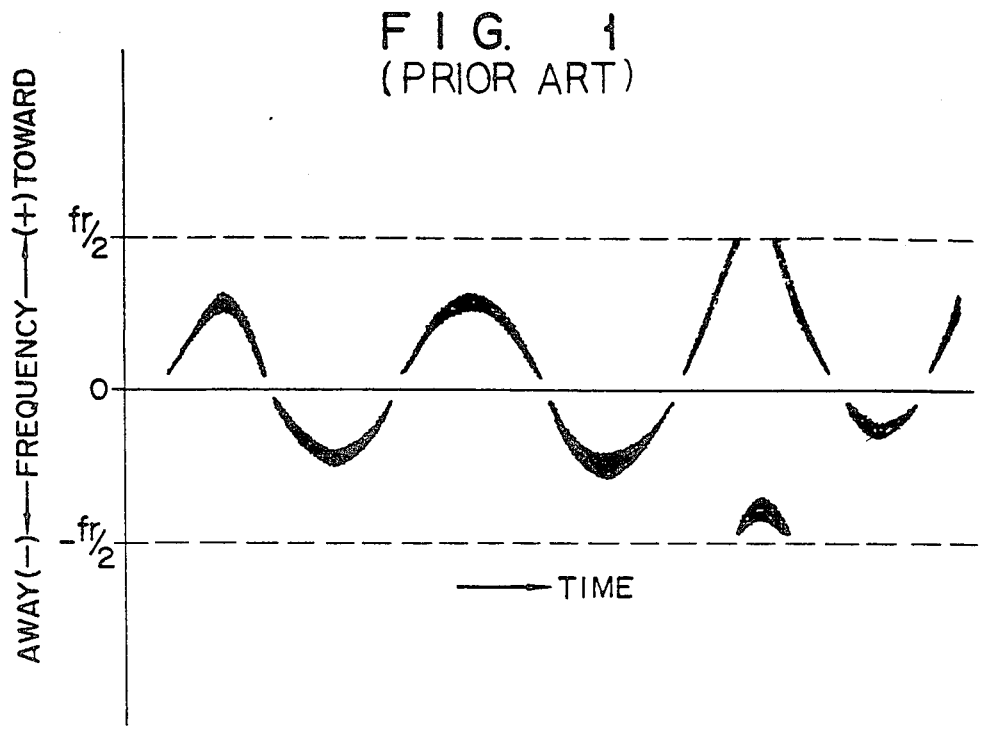
FIG. 1 shows a blood flow signal waveform obtained by a prior pulsed ultrasound Doppler blood flow sensing device.
Figure 2:
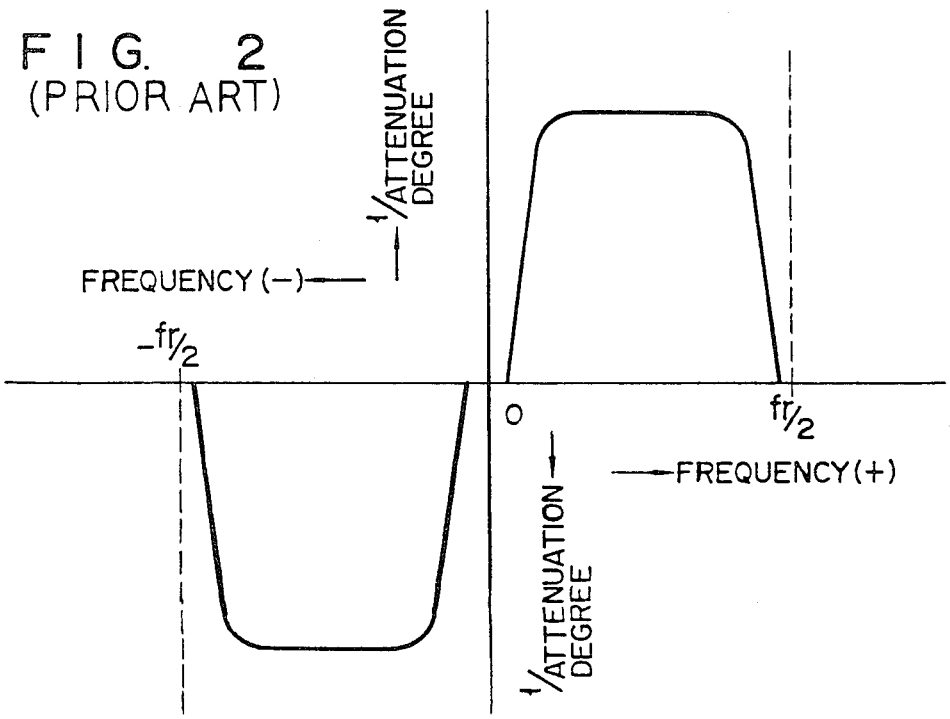
FIG. 2 shows a band pass characteristic of a band pass filter used in the prior device for providing a blood flow signal waveform as shown in FIG. 1.

The stable reference signal oscillator 1 oscillates a reference clock pulse signal at frequency $4f_o$, for example, 10 MHz. $f_o$ indicates the frequency of the output signal from the second frequency divider 3, and is used as a reference frequency for the signal at a rate frequency produced from the fourth frequency divider 5. The reference clock pulse signal is applied to the first frequency divider 2 where its frequency is divided into $2f_o$ (5 MHz). The Q and $\overline{Q}$ output signals from the first frequency divider 2, which are phased with $\pi/4$, are applied to the second and third frequency dividers 3 and 4 where their frequencies are divided into $f_o$ (2.5 MHz). The divided frequency $f_o$ is used as a reference for the rate frequency of the signal generated by the fourth frequency divider 5. The output signal from the second frequency divider 3 is applied to the fourth frequency divider 5 and to the first input terminal of the range gate 12. The output signal from the second frequency divider 3 is frequency-divided into a signal at the 1/N frequency (N is an integer). For example, when N is 500, the output signal from the fourth frequency divider 5 has the frequency of $f_o/(2\times 500)$ or 5 KHz. The output signal from the fourth frequency divider 5 is applied as a rate frequency signal to the pulser 6, and to the second input terminal of the range gate circuit 12. The pulser 6 receives the rate frequency signal from the frequency divider 5 to produce a drive pulse of 2.5 KHz at the same rate. The transducer 7, upon receipt of the drive pulse, radiates ultrasonic pulses of 2.5 KHz at the same rate, or 5 KHz. The ultrasonic pulses emitted from the transducer 7 disposed on the organism P are injected into the organism P and directed at a portion in the organism with a different acoustic impedance, for example, blood corpuscles. In this case, since the blood corpuscles are moving, the echoes of the ultrasound pulses have shifted in frequency due to the Doppler effect. The echoes returned from various portions in the organism are received by the transducer 7 where these are converted into an electrical signal. The converted electrical signal is applied to the amplifier 8 for its amplification. The amplified signal is applied to the first and second mixers 9a and 9b which have been supplied with the output signals at the same frequency $f_o$ (2.5 MHz) but different phases of $\pi/4$ from the frequency dividers 3 and 4. These mixers 9a and 9b respectively mix these input signals for discriminating the "foward" and "away" directional signals. The mixed signals from the mixers 9a and 9b are respectively passed through the low pass filters 10a and 10b, where their high frequency component which are unnecessary for measuring the blood flow are removed. Then, the output signals from the low pass filters 10a and 10b are applied to the sample/hold circuits 11a and 11b. These sample/hold circuits are driven by the output signal from the range gate circuit 12 for a specific period from a specific time. The period and the sampling start time are given by the gate signal from the range gate signal from the range gate circuit 12. More specifically, the time that the echo signal reaches the transducer 7 is proportional to the range of travel of the rate pulse, i.e., the depth of a portion of the organism which is reflecting the injected ultrasound pulse. Accordingly, if the sample/hold circuits 11a and 11b begin to be driven at the arrival time of the echo of the ultrasound reflected from the reflecting portion, and their operation is continued for a given period of time corresponding to a width of the portion, for example, a diameter of a blood vessel through which blood under measurement flows, these circuits can extract only the echo pulses returned from that portion through their sampling and holding operations. It is for this reason that the range gate circuit 12 is provided. The range gate circuit 12 produces a pulse signal with a pulse width corresponding to the width of the portion being observed at a time corresponding to the depth of the portion. The circuit with such a function can readily be realized using a counter which starts its counting operation and produces that pulse when its count reaches a predetermined count corresponding to the depth of the portion under measurement. The output signals thus sampled and held are applied to the frequency analyzer 14 where these signals are analyzed within a frequency range $\pm f_r/2$, and separated into the "foward" and "away" directional signals, as mentioned above. These processed signals are produced from the analyzer 14 in the form of positive and negative signals. These signals are digitally processed in the signal processing circuit 15 for effecting the following display in the next stage display device 16. In the display, unlike the display in FIG. 1 where the frequency components $\pm f_r/2$ are displayed in the areas $\pm f_r/2$, the frequency components 0 to $+f_r/2$ are displayed in the area from $-f_r$ to $-f_r/2$; the frequency components similar to those in FIG. 1 in the area from $-f_r/2$ to $+f_r/2$; the frequency components $-f_r/2$ to 0 in the area from $+f_r/2$ to $+f_r$. These signals may be displayed in the usual manner, that is, where the intensity modulation is applied to the scanning line swept in the direction of the frequency axis, as in the usual Doppler frequency analysis display. According to this method, two harmonic components are concurrently displayed with a separation of an exact $f_r$, and the waveform crossing the center (frequency 0) is displayed continuously from $-f_r$ to $+f_r$. No problem in a practical observation arises from such display, however. An operator can clearly distinguish the reference frequency signal from these harmonic components based on his experience with several clinical cases.

As described above referring to FIG. 4, the band pass filters 13a and 13b each have a frequency characteristic in which the attenuation curve is flat over a wide frequency range including the frequencies of $\pm f_r/2$, where the blood flow signal is extremely attenuated in the prior blood flow measuring device and, up to $\pm f_r$. Further, the frequency characteristic of the display device 16 is selected so as to cover the frequencies up to $\pm f_r$. These features eliminate the discontinuity in the display in the frequency region of $\pm f_r$. The continuous display, as a natural consequence, provides for an easy reading of the blood flow on the display screen and reduces the chance of erroneous readings. The blood flow measuring device according to the present invention can display the blood flow over a frequency range twice that of the prior art, using the same rate frequency as that of the latter. Thus, the doctor can observe the blood flow signal at a frequency within $\pm f_r$, which is two times that limited by the sampling formula, on the basis of his experience with the organism signals.

Although the frequency range of the blood flow signal, which can be observed, is doubled compared to the prior art, the frequency range of the blood flow signal analyzed or operated by the frequency analyzer 14 is $\pm f_r/2$, in other words, the same as that of the prior art. Accordingly, the frequency analyzer 14 used in the present invention may be one with the same speed and function as those of the conventional one. No specially designed frequency analyzer is required for the present invention. Alternatively, the frequency range of $\pm f_r/2$ analyzed by the circuit 14 may be expanded to $\pm f_r$. Further, the frequency range of $\pm f_r$ of the display frequency characteristic may be $\pm nf_r/2$ where n is an integer.

Figure 5:
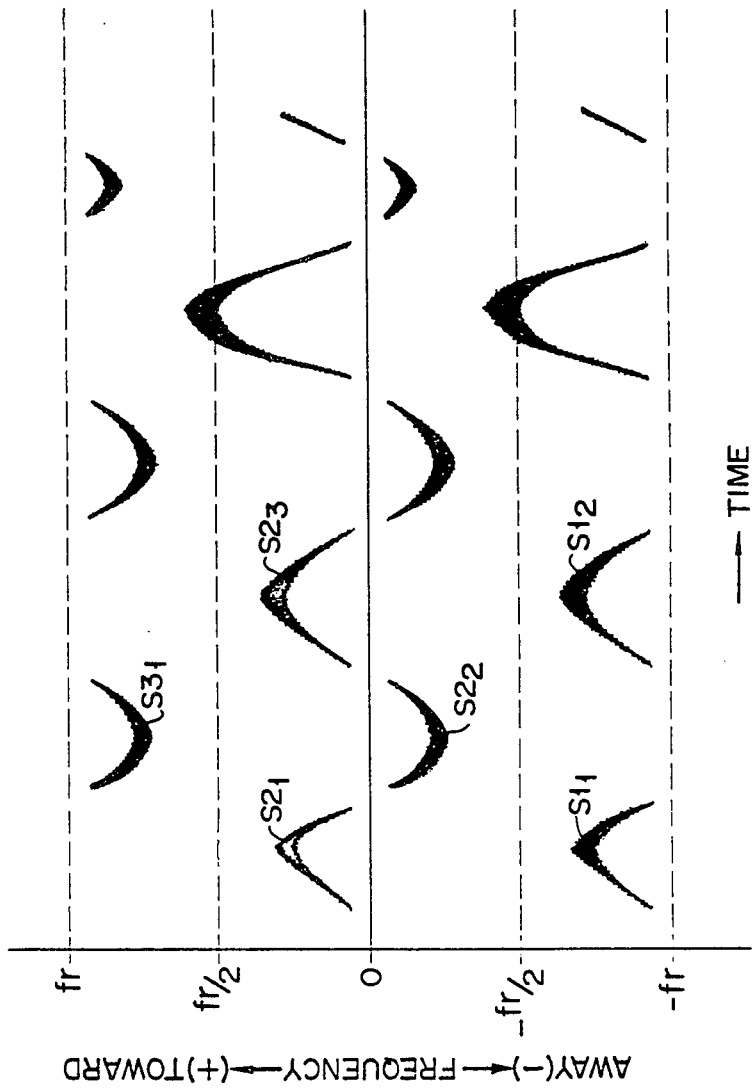
FIG. 5 shows a set of waveforms of a blood flow signal provided by the FIG. 3 blood flow sensing device.

While the blood flow signals are displayed separated by an exact $f_r$ in the above-mentioned embodiment, either of them can be erased on the display screen in a manner that in a scanning direction from $-f_r$ to $+f_r$, for example, as for the first and second signals exactly separated by $f_r$, the former is subtracted from the latter. More explicitly, in FIG. 5, the signal $S1_1$ is subtracted from the signal $S2_1$. The result is that the signal $S1_1$ is displayed and the signal $S2_1$ is not displayed. When the signal $S1_1$ crosses the frequency $-f_r$, the signal $S2_2$ is first displayed and then the signal $S3_1$ is displayed. In this case, the signal $S2_2$ is subtracted from the signal $S3_1$. The result is that the signal $S3_1$ is not displayed but only the signal $S2_2$. Then, the signal $S2_2$ crosses the frequency 0. At this time, the signal $S1_2$ is first detected and hence is displayed, and the signal $S2_3$ secondly detected is not displayed. In this way, only the signals $S1_1, S2_2, S1_2, \ldots$ are displayed on the display screen. As seen from the figure, a train of the signals S1 ($S1_1, S1_2, \ldots$) and another train of the signals S2 ($S2_1, S2_2, \ldots$) are separated by $f_r$ and these are not continuous on the display. The continuous display, however, can be obtained by using an algorithm that when the signal S2 first detected approaches the frequency 0, even when the signal crosses the frequency 0, it is prohibited from moving to the signal S1 near $-f_r$. If this algorithm is employed, the train of the signals S are continuously displayed.

It should be understood that the present invention may variously be changed and modified within the scope of the appended claims.

What is claimed is:

1. A plused ultrasound Doppler blood flow sensing device comprising:
   rate pulse signal generating means for producing a rate pulse signal at a rate frequency $f_r$;
   drive pulses signal generating means for producing a drive pulse signal in response to said rate pulse signals;
   transducing means for emitting ultrasound pulses into an object under diagnosis in response to a drive pulse signal from said drive pulse signal generating means and for converting echos of the ultrasonic pulses returning from said object into electrical signal;
   sampling and holding means for sampling and holding only the electrical signals of the echos returning from positions at a given depth of said object, said sampling occuring at a sampling rate $f_r$;
   band pass filter means for extracting only the Doppler frequency shift signals from the sampled and held signals, said band pass means passing components of said sampled and held signals between 0 and $+f_r$;

frequency analyzing circuit for analyzing the frequencies of said doppler frequency shift signals;

signal processing means for processing said frequency analyzed Doppler frequency shift signals to obtain Doppler shifts; and display means for displaying blood flow signals represents said obtained Doppler frequency shifts and have frequencies at least between the frequencies $-f_r$ and $+f_r$.

2. A pulsed ultrasonic Doppler blood flow sensing device according to claim 1, in which said frequency analyzing circuit analyze frequencies within at least a frequency range between $-f_r/2$ and $+f_r/2$.

3. A pulsed ultrasonic Doppler blood flow sensing device according to claim 1 or 2, in which said display means displays a blood flow signal at a frequency within a frequency range between $-nf_r/2$ and $+nf_r/2$ (n is an integer).

* * * * *